(12) United States Patent
Burdette et al.

(10) Patent No.: US 9,962,564 B2
(45) Date of Patent: *May 8, 2018

(54) ULTRASOUND DEVICE AND METHOD FOR TREATMENT OF A TARGET NERVE CONTAINED IN INTERVERTEBRAL TISSUE

(71) Applicant: Acoustic MedSystems, Inc., Champaign, IL (US)

(72) Inventors: Everette C. Burdette, Champaign, IL (US); Dana Deardorff, Oakland, CA (US)

(73) Assignee: ACCOUSTIC MEDSYSTEMS, INC., Savoy, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/841,586

(22) Filed: Aug. 31, 2015

(65) Prior Publication Data
US 2015/0367147 A1 Dec. 24, 2015

Related U.S. Application Data

(63) Continuation of application No. 13/657,464, filed on Oct. 22, 2012, now Pat. No. 9,119,954, which is a (Continued)

(51) Int. Cl.
*A61B 8/00* (2006.01)
*A61N 7/02* (2006.01)
(Continued)

(52) U.S. Cl.
CPC ...... *A61N 7/02* (2013.01); *A61B 2017/00261* (2013.01); *A61N 2007/0021* (2013.01); *A61N 2007/0078* (2013.01)

(58) Field of Classification Search
CPC .... A61B 2017/0026; A61N 2007/0021; A61N 2007/0078; A61N 7/02
See application file for complete search history.

(56) References Cited

U.S. PATENT DOCUMENTS 4,326,529 A   4/1982 Doss et al.
4,976,709 A   12/1990 Sand
(Continued)

OTHER PUBLICATIONS

Chopra et al., MRI-compatible transurethral ultrasound system for the treatment of localized prostate cancer using rotational control Medical Physics, vol. 35, No. 4, pp. 1346-1357, Apr. 2008.
(Continued)

*Primary Examiner* — Baisakhi Roy
(74) *Attorney, Agent, or Firm* — Foley & Lardner LLP

(57) ABSTRACT

A minimally invasive applicator device for treatment of intervertebral tissue containing at least one target nerve includes an insertion device having a proximal end and a distal end for insertion into the intervertebral tissue containing at least one target nerve, an ultrasound transducer device coupled to the distal end of the insertion device, and an external RF power generator electrically that provides power to the ultrasound transducer device. The ultrasound transducer device includes an array of a plurality of transducer crystals which are all aligned along a line defined by an axis enclosed by each of the plurality of transducer crystals disposed sequentially and longitudinally adjacent each other along the axis to form a customized flexible array along the applicator device. Ultrasound radiative output treatment outward from the axis of the transducer crystals allows for treatment of the intervertebral tissue containing at least one target nerve.

23 Claims, 1 Drawing Sheet

Related U.S. Application Data continuation of application No. 11/818,046, filed on Jun. 12, 2007, now Pat. No. 8,292,815, which is a continuation of application No. 10/230,949, filed on Aug. 29, 2002, now abandoned.

(60) Provisional application No. 60/315,841, filed on Aug. 29, 2001.

(51) Int. Cl.
 *A61B 17/00* (2006.01)
 *A61N 7/00* (2006.01)

(56) References Cited

U.S. PATENT DOCUMENTS

| | | | |
|---|---|---|---|
| 5,057,104 A | 10/1991 | Chess | |
| 5,143,063 A | 9/1992 | Fellner | |
| 5,391,197 A | 2/1995 | Burdette et al. | |
| 5,471,988 A * | 12/1995 | Fujio | A61B 8/12 600/439 |
| 5,522,869 A | 6/1996 | Burdette et al. | |
| 5,533,401 A | 7/1996 | Gilmore | |
| 5,549,638 A * | 8/1996 | Burdette | A61N 7/02 310/322 |
| 5,620,479 A * | 4/1997 | Diederich | A61B 18/18 601/3 |
| 5,810,801 A | 9/1998 | Anderson et al. | |
| 5,849,029 A | 12/1998 | Eckhouse et al. | |
| 5,964,749 A | 10/1999 | Eckhouse et al. | |
| 6,049,159 A | 4/2000 | Barthe et al. | |
| 6,050,943 A | 4/2000 | Slayton et al. | |
| 6,113,559 A | 9/2000 | Klopotek | |
| 6,254,553 B1 * | 7/2001 | Lidgren | A61N 7/02 600/438 |
| 6,258,086 B1 | 7/2001 | Ashley et al. | |
| 6,325,769 B1 | 12/2001 | Klopotek | |
| 6,350,262 B1 * | 2/2002 | Ashley | A61B 18/08 606/32 |
| 6,350,276 B1 | 2/2002 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,394,956 B1 | 5/2002 | Chandrasekaran et al. | |
| 6,405,090 B1 | 6/2002 | Knowlton | |
| 6,413,255 B1 | 7/2002 | Stern | |
| 6,425,912 B1 | 7/2002 | Knowlton | |
| 6,430,446 B1 | 8/2002 | Knowlton | |
| 6,438,424 B1 | 8/2002 | Knowlton | |
| 6,461,378 B1 | 10/2002 | Knowlton | |
| 6,470,216 B1 | 10/2002 | Knowlton | |
| 6,575,969 B1 | 6/2003 | Rittman et al. | |
| 6,595,934 B1 | 7/2003 | Hissong et al. | |
| 6,626,902 B1 | 9/2003 | Kucharczyk et al. | |
| 6,673,063 B2 | 1/2004 | Brett | |
| 6,726,684 B1 | 4/2004 | Woloszko et al. | |
| 6,929,640 B1 | 8/2005 | Underwood et al. | |
| 6,980,862 B2 * | 12/2005 | Fredricks | A61B 18/1482 606/27 |
| 7,270,658 B2 | 9/2007 | Woloszko et al. | |
| 7,331,956 B2 * | 2/2008 | Hovda | A01N 43/52 606/32 |
| 7,462,178 B2 | 12/2008 | Woloszko et al. | |
| 7,473,224 B2 * | 1/2009 | Makin | A61B 8/12 600/437 |
| 7,806,892 B2 * | 10/2010 | Makin | A61B 8/12 600/424 |
| 8,292,815 B2 * | 10/2012 | Burdette | A61N 7/02 600/437 |
| 2001/0003791 A1 | 6/2001 | Burbank et al. | |
| 2001/0031922 A1 | 10/2001 | Weng et al. | |
| 2002/0016546 A1 * | 2/2002 | Cerofolini | A61B 8/14 600/443 |
| 2002/0035361 A1 | 3/2002 | Houser et al. | |
| 2002/0095144 A1 * | 7/2002 | Carl | A61B 18/02 606/21 |
| 2002/0151940 A1 | 10/2002 | Bar-Cohen et al. | |
| 2003/0013960 A1 | 1/2003 | Makin et al. | |
| 2003/0014093 A1 | 1/2003 | Makin | |
| 2003/0032898 A1 | 2/2003 | Makin et al. | |
| 2003/0069569 A1 | 4/2003 | Burdette et al. | |
| 2003/0130598 A1 | 7/2003 | Manning et al. | |
| 2003/0163067 A1 * | 8/2003 | Lidgren | A61B 6/12 601/2 |
| 2005/0015024 A1 | 1/2005 | Babaev | |
| 2005/0036976 A1 | 2/2005 | Rubin et al. | |
| 2005/0090816 A1 * | 4/2005 | McClurken | A61B 17/32 606/41 |
| 2005/0228318 A1 | 10/2005 | Iger | |
| 2005/0261584 A1 | 11/2005 | Eshel et al. | |
| 2006/0074314 A1 | 4/2006 | Slayton et al. | |
| 2006/0074355 A1 | 4/2006 | Slayton et al. | |
| 2006/0241436 A1 | 10/2006 | Sunnanvader | |
| 2007/0016062 A1 * | 1/2007 | Park | A61M 25/0158 600/459 |
| 2008/0004614 A1 | 1/2008 | Burdette et al. | |
| 2008/0125674 A1 | 5/2008 | Bilecen et al. | |
| 2009/0018446 A1 | 1/2009 | Medan et al. | |
| 2010/0312096 A1 | 12/2010 | Guttman et al. | |

OTHER PUBLICATIONS

Diederich et al, Catheter-Based Ultrasound Devices and MR Thermal Monitoring for Conformal Prostate Thermal Therapy, 30th Annual International IEEE EMBS Conference, Vancouver, British Columbia, Canada, Aug. 20-24, 2008, pp. 3664-3668.

Diederich et al., An Improved Bolus Configuration for Commercial Multielement Ultrasound and Microwave Hyperthermia Systems, Med. Phys. 21(9), Sep. 1994, pp. 1401-1403, Am. Assoc. Phys. Med.

Diederich et al., Transurethral Ultrasound Applicators with Directional Heating Patterns for Prostate Thermal Therapy: In Vivo Evaluation Using Magnetic Resonance Thermometry, Med. Phys. 31(2), Feb. 2004, pp. 1-9, Am. Assoc. Phys. Med.

European Office Action for EPO Application 08745765.1, dated Jan. 23, 2013, 5 pages.

International Preliminary Report on Patentability for PCT Application No. PCT/US2013/055196, dated Feb. 17, 2015, 7 pages.

International Search Report and Written Opinion for Application No. PCT/US52013/055196, dated Nov. 12, 2013, 13 pages.

Prakash, et al., Patient Specific Optimization-Based Treatment Planning for Catheter-Based Ultrasound Hyperthermia and Thermal Ablation, Proceedings of SPIE, vol. 7181 71810E, Feb. 2009, 10 pages.

Prionas et al., Temperature Distributions Induced in Pig Tissues by a Water-Cooled Disk Electrode rf System, Med. Phys. 11(1), Jan./Feb. 1984, pp. 22-25, Am. Assoc. Phys. Med.

Restriction Requirement for U.S. Appl. No. 11/744,773, dated Oct. 28, 2009, 8 pages.

Ross et al., Highly directional transurethral ultrasound applicators with rotational control for MRI-guided prostatic thermal therapy, Physics in Medicine and Biology, vol. 49, No. 2, pp. 189-204, Jan. 21, 2004.

U.S. Notice of Allowance for U.S. Appl. No. 11/818,046, dated Jun. 21, 2012, 7 pages.

U.S. Notice of Allowance for U.S. Appl. No. 13/657,464, dated Apr. 24, 2015, 7 pages.

U.S. Office Action for U.S. Appl. No. 10/230,949, dated Mar. 22, 2006, 6 pages.

U.S. Office Action for U.S. Appl. No. 11/744,773, dated Apr. 2, 2014, 10 pages.

U.S. Office Action for U.S. Appl. No. 11/744,773, dated Dec. 12, 2014, 10 pages.

U.S. Office Action for U.S. Appl. No. 11/744,773, dated Mar. 5, 2010, 8 pages.

U.S. Office Action for U.S. Appl. No. 11/744,773, dated Nov. 12, 2010, 10 pages.

(56) References Cited

OTHER PUBLICATIONS

U.S. Office Action for U.S. Appl. No. 11/744,773, dated Oct. 11, 2013, 12 pages.
U.S. Office Action for U.S. Appl. No. 11/744,773, dated Jul. 10, 2015, 11 pages.
U.S. Office Action for U.S. Appl. No. 11/818,046, dated Jul. 23, 2009, 7 pages.
U.S. Office Action for U.S. Appl. No. 11/818,046, dated Apr. 14, 2010, 11 pages.
U.S. Office Action for U.S. Appl. No. 11/818,046, dated Dec. 28, 2010, 8 pages.
U.S. Office Action for U.S. Appl. No. 11/818,046, dated Oct. 5, 2011, 9 pages.
U.S. Office Action for U.S. Appl. No. 12/004,753, dated Apr. 12, 2010, 7 pages.
U.S. Office Action for U.S. Appl. No. 12/004,753, dated Sep. 25, 2009, 7 pages.
U.S. Office Action for U.S. Appl. No. 13/657,464, dated Mar. 13, 2014, 13 pages.
U.S. Office Action for U.S. Appl. No. 13/657,464, dated Sep. 29, 2014, 14 pages.
Office Action for U.S. Appl. No. 11/744,773, dated Aug. 11, 2016, 13 pages.
U.S. Office Action for U.S. Appl. No. 11/744,773, dated Mar. 11, 2016, 16 pages.
Final Office Action in U.S. Appl. No. 11/744,733, dated Aug. 10, 2017, 18 pages.
Office Action in U.S. Appl. No. 14/421,902, dated Jul. 28, 2017, 11 pages.

\* cited by examiner

ULTRASOUND DEVICE AND METHOD FOR TREATMENT OF A TARGET NERVE CONTAINED IN INTERVERTEBRAL TISSUE

CROSS-REFERENCE TO RELATED PATENT APPLICATIONS

This application is a continuation and claims priority from copending U.S. patent application Ser. No. 11/818,046 filed Jun. 12, 2007, which is a continuation of U.S. patent application Ser. No. 10/230,949 filed Aug. 29, 2002, which claims priority from U.S. Provisional Patent Application Ser. No. 60/315,841. The entire contents of all three applications are herein incorporated by reference in their entirety.

FIELD OF THE INVENTION

The present invention relates generally to ultrasound applicator devices. More particularly, the present invention relates to the structure, design and use of a minimally invasive ultrasound applicator device for the thermal treatment and repair of intervertebral disc tissue.

BACKGROUND OF THE INVENTION

The concept of using heat to treat degenerated disc tissue is conventionally known. For example, the orthopedic company ORATEC Interventions, Inc. has developed and marketed a device for thermal spine treatment based on Intra-Discal Electro-Thermal (IDET) technology. IDET technology involves a minimally invasive catheter using RF induction of a hot-wire tip for thermal conduction.

While relatively straightforward in design and use, the ORATEC device is very limited in thermal capabilities and ultimately in treatment efficacy. The region of disc tissue that is heated with this device is quite small with a sharp temperature fall-off from the surface of the catheter tip (therapeutic temperature elevation in the tissue is estimated to be only 1-3 mm from the catheter). As a result, the treatment itself is likely limited in effectiveness for any given patient, simply because the volume of tissue that is heated is not large enough to produce a significant therapeutic effect (i.e., shrinkage of collagen fibers, destruction of invading nerves, and/or reduction of pressure on the spinal nerves).

Furthermore, the design and treatment approach of the IDET catheter is significantly limiting in the general treatment population—it is estimated that more than 50% of the potential treatment population is not even a candidate for this device therapy. This is due to the use of a flexible "navigable catheter" which must be circumnavigated around the disc border between the annulus and the nucleus, positioning the treatment tip back at the posterior region of the degenerated disc. This positioning is possible with a healthy or slightly degenerated disc because the fibers of the annulus help "steer" the catheter around the disc tissue. However, with greater disc degeneration, this positioning is not possible because of the tissue degradation; there is no structure for the catheter to steer around, providing the danger of slippage and puncturing the opposite wall. As a result, the majority of patients, especially those with advanced degeneration or herniation, cannot be treated with this approach.

SUMMARY OF THE INVENTION

It is therefore an object of the invention to provide a treatment device which provides a significant improvement both in the thermal capabilities and therapeutic effects for disc tissue.

It is another object of the invention to provide a treatment device which can be used on an increased percentage of the potential treatment population and disease states.

It is yet another object of the invention to provide an ultrasound device that can effectively heat an increased volume of tissue for greater therapeutic effect.

It is still another object of the invention to provide an ultrasound device and treatment approach that allows for treatment during more advanced stages of disc degeneration.

It is finally another object of the invention to provide a robust design for an ultrasound device during insertion while also providing for improved directional control.

Further advantages and features of the present invention will be apparent from the following specifications and claims illustrating the preferred embodiments of the present invention.

DETAILED DESCRIPTION OF THE INVENTION

Figure 1:
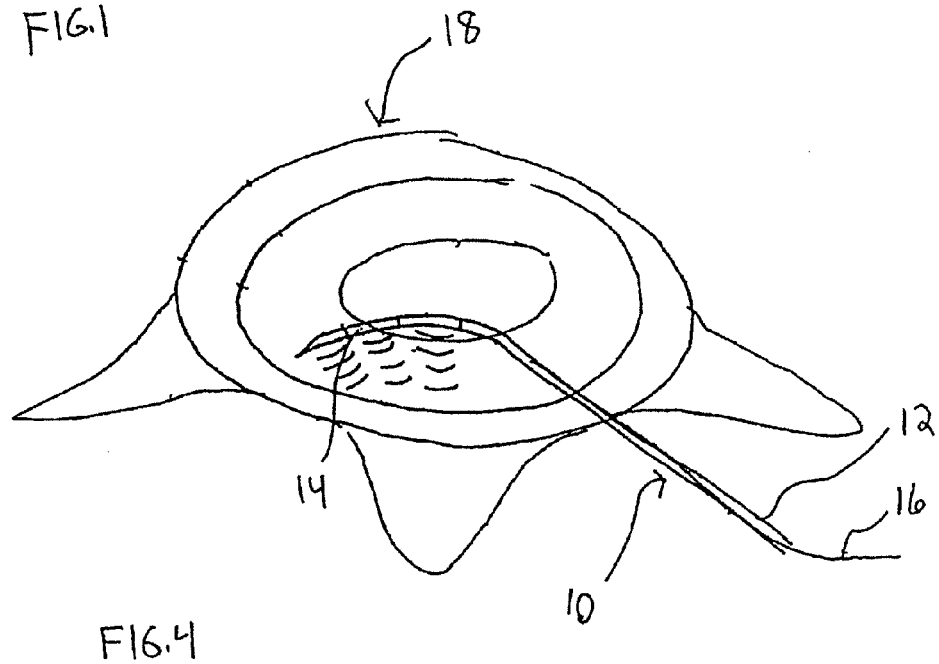
FIG. 1 is a perspective view of the ultrasound device according to one embodiment of the invention as it is positioned and maneuvered within the spinal body.

The present invention includes an applicator comprising a catheter and/or a needle with a distal tip for direct insertion into the tissue of the intervertebral disc. At the distal tip of the applicator is one or more ultrasound transducer crystals for producing high-powered ultrasound energy to be transmitted and absorbed in the disc tissue. In one embodiment of the invention, energy for the ultrasound transducer(s) is produced by an external RF power generator and delivered through electrical wires connected to the applicator. Small thermocouples can be placed on the ultrasound transducer/applicator and/or in the surrounding tissue to monitor the temperature. Means are also provided for active cooling of the ultrasound transducers by circulating flow of liquid or gas within the applicator.

The treatment process is initiated with the placement of the applicator device into the posterior region of the intervertebral disc tissue. The positioning of the applicator to the selected region of disc degeneration is guided via on-line diagnostic imaging, such as intra-operative fluoroscopic imaging. Power to the ultrasound device is then produced at a level to provide significant temperature elevation of the surrounding disc tissue. In one embodiment of the invention, the temperature elevation is greater than 60° C. for the targeted tissue. The temperature elevation is intended to shrink the collagen fibers in the surrounding tissue of the annulus fibrosus, and/or destroy small nerves that may have invaded and innervated the surrounding degenerated tissue, and/or provide greater structural integrity and disc support for the fragmented nucleus pulposus to relieve pressure on the spinal nerves.

Although these therapeutic effects are intended primarily for treatment of disc degeneration and herniation, this treatment approach with the ultrasound device may also be useful for other symptomatic spinal problems causing back pain, leg pain, etc. Additionally, the ultrasound device may be used to thermally shrink and/or seal the entrance hole and any subsequent unwanted tissue damage upon removal of the applicator from the disc tissue. In another embodiment of the device, the ultrasound transducers may also be used for diagnostic imaging to guide and monitor the treatment process.

The improvements described herein result primarily from the fundamental advantages of ultrasound propagation and heating of soft tissue. The effective energy delivery into the tissue allows for thermal treatment of larger tissue volumes in shorter times. Furthermore, the ultrasound device can be designed to provide selective control of the energy delivery to target and treat a specific region of tissue, dynamically controlling both the size and shape of the thermal treatment region. Extensive research and development activities have previously been completed on such ultrasound devices, and prototype applicators prepared for clinical application have demonstrated the feasibility of this approach.

FIG. 1 shows the ultrasound device positioned in the spinal body according to one embodiment of the invention. The ultrasound device, shown generally at 10, comprises a catheter or needle 12 with a plurality of ultrasound transducer crystals 14 at one end thereof. A guidewire 16 can be placed within the catheter or needle 12 for controlling the direction of the ultrasound device 10 inside the spinal body, shown generally at 18.

Figure 2:
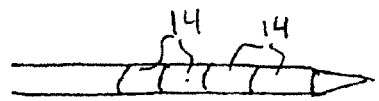
FIG. 2 is a side view of a plurality of segmented transducer elements with individual power control according to one embodiment of the invention.
Figure 3:
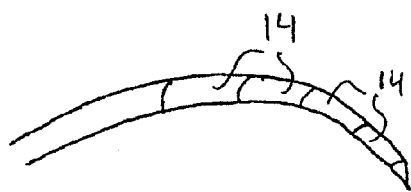
FIG. 3 is a side view of an alternate embodiment of the invention showing a curved array of transducer elements.

FIGS. 2-3 show different embodiments of the individual transducer crystals 14. FIG. 2 shows a plurality of segmented transducer crystals 14. Depending upon the particular system and procedure requirements, it is possible for each of the transducer crystals 14 to have individual power control. The embodiment shown in FIG. 3 discloses a curved array of transducer crystals 14. It is possible for the array of transducer crystals 14 to be permanently curved. Alternatively, the array could be flexible based upon the direction and shape of the guidewire 16.

Figure 4:
FIG. 4 is a cross-sectional view of a transducer element according to one embodiment of the invention.
Figure 5:
FIG. 5 is a cross-sectional view of a transducer element according to another embodiment of the invention.
Figure 6:
FIG. 6 is a cross-sectional view of an individual transducer element according to yet another embodiment of the invention.

FIGS. 4-6 show different potential cross-sectional shapes for the transducer crystals 14. FIG. 4 discloses a transducer crystal 14 with a cylindrically shaped cross-section. It is possible for the transducer crystal 14 to include or not include angular sectoring. FIG. 5 shows the transducer crystal as having a curvi-linear cross-section. This transducer crystal 14 could have a focused or defocused cross-section, depending on the direction of activation of ultrasound energy. The transducer crystal of FIG. 6 has a substantially planar cross-section. Transducer crystals 14 having cross-sections of other shapes are also possible without departing from the invention's broader aspects.

Additionally, the ultrasound device 10 could use a cooling method, either actively or passively, in order to remove thermal waste energy from the transducer crystal and improve the device's power and performance.

While the preferred embodiments of the invention have been described, it will be understood by those skilled in the art to which the invention pertains that numerous modifications and changes may be made without departing from the true spirit and scope of the invention. It is accordingly intended to define the scope of the invention precisely in the claims appended to and forming a part of this application.

The invention claimed is:

1. A minimally invasive applicator device for treatment of intervertebral tissue containing at least one target nerve, comprising:
   an insertion device having a proximal end and a distal end for insertion into the intervertebral tissue containing at least one target nerve, the insertion device being structurally robust for direct insertion into the intervertebral tissue without damage or misalignment;
   an ultrasound transducer device coupled to the distal end of the insertion device, wherein the ultrasound transducer device includes an array of a plurality of transducer crystals arranged in a straight line defined by an axis enclosed by each of the plurality of transducer crystals disposed sequentially and longitudinally adjacent each other along the axis to form a customized flexible array along the applicator device, thereby enabling ultrasound radiative output treatment outward from the axis of the transducer crystals of a treatment region of specific size and shape of the intervertebral tissue containing at least one target nerve; and
   an external RF power generator electrically connected to the ultrasound transducer device, the generator providing power to the ultrasound transducer device,
   wherein each of the plurality of transducer crystals has a curvilinear cross-section or a planar cross-section, and
   wherein each of the plurality of transducer crystals has a non-circular cross-section.

2. The device of claim 1, wherein the insertion device comprises a catheter or needle.

3. The device of claim 2, wherein the ultrasound transducer device includes at least one individual electrical power connection and control element.

4. The device of claim 3, wherein the plurality of transducer crystals include an individual electrical power connection.

5. The device of claim 2, further comprising means to cool internal transducer heating from the plurality of transducer crystals by circulating a flow of a liquid or gaseous coolant through the applicator device.

6. The device of claim 2, wherein the ultrasound transducer crystal is configured to provide positioning visualization ultrasound imaging of the at least one target nerve and surrounding intervertebral tissue.

7. The device of claim 1, wherein each of the plurality of ultrasound transducer crystals are substantially planar.

8. The device of claim 1, wherein the plurality of ultrasound transducer crystals are sectioned electrically and/or mechanically to provide separate active elements within at least one of the ultrasound transducer crystals.

9. The device of claim 1, further comprising a thermocouple placed on or adjacent to at least one of the ultrasound transducer crystals, the thermocouple monitoring the surface temperature of the device and/or the temperature of the intervertebral tissue/device interface.

10. The device of claim 1, further comprising a thermocouple placed within the intervertebral tissue containing at least one target nerve to monitor the temperature of the treatment region of the intervertebral tissue.

11. The device of claim 10, wherein the thermocouple is deployed into the intervertebral tissue containing at least one target nerve from the applicator device.

12. The device of claim 1, further comprising a separate insertion tool or sheath for introduction into intervertebral tissue containing at least one target nerve, and wherein the applicator device is inserted into the tissue through the lumen of the insertion tool or sheath.

13. The device of claim 12, wherein the insertion tool comprises a predetermined fixed shape, and wherein the applicator device is flexible to accommodate the fixed shape in its passage into the intervertebral tissue containing at least one target nerve.

14. The device of claim 1, wherein the distal end of the applicator device is fixedly curved to provide enhanced accessibility of the ultrasound transducer to a posterior region of intervertebral tissue containing at least one target nerve.

15. The device of claim 1, wherein the region is a diseased region.

16. A method for treating at least one target nerve contained in intervertebral tissue comprising a thermal treatment region having a specific volume, the method comprising the steps of:
    inserting, positioning, and guiding an applicator device into the intervertebral tissue containing at least one target nerve via diagnostic imaging with an applicator device comprising a plurality of ultrasound transducer crystals having controlled size and shape to generate a custom size and shape for the thermal treatment region having the specific volume, wherein the plurality of ultrasound transducer crystals are arranged in a straight line defined by a longitudinal axis of the plurality of transducer crystals disposed sequentially adjacent each other along the longitudinal axis, wherein each of the plurality of transducer crystals has a curvilinear cross-section or a planar cross-section, and wherein each of the plurality of transducer crystals has a non-circular cross-section;
    applying power to at least one ultrasound transducer of the applicator device, the at least one ultrasound transducer heating the thermal treatment region comprised of the intervertebral tissue containing at least one target nerve;
    removing the applicator device from the intervertebral tissue.

17. The method of claim 16, wherein the applicator device is positioned and guided using at least one of intra-operative fluoroscopic imaging and one of diagnostic ultrasound imaging.

18. The method of claim 16, wherein the diagnostic imaging comprises ultrasound imaging provided by the transducer crystals located within the applicator device.

19. The method of claim 16, further comprising the step of measuring the temperature on the applicator device and/or in surrounding tissue, wherein a temperature sensor is integrated with the applicator device.

20. The method of claim 16, further comprising the step of heating an entrance hole with the applicator device in order to produce thermal sealing or shrinking of the at least one target nerve upon removal of the applicator device.

21. The method of claim 16, wherein the transducer heating is controlled by varying the power, frequency, or duration of an applied signal to each of the transducer crystals.

22. The method of claim 16, further comprising the step of delivering a drug or therapeutic agent into the at least one target nerve to enhance the therapeutic effect of the thermal energy delivery.

23. A minimally invasive applicator device for treatment of intervertebral tissue containing at least one target nerve, comprising:
    an insertion device having a proximal end and a distal end for insertion into the intervertebral tissue containing at least one target nerve, the insertion device being structurally robust for direct insertion into the intervertebral tissue without damage or misalignment;
    an ultrasound transducer device coupled to the distal end of the insertion device, wherein the ultrasound transducer device includes an array of a plurality of transducer crystals arranged in a straight line defined by an axis enclosed by each of the plurality of transducer crystals disposed sequentially and longitudinally adjacent each other along the axis to form a customized flexible array along the applicator device, thereby enabling ultrasound radiative output treatment outward from the axis of the transducer crystals of a treatment region of specific size and shape of the intervertebral tissue containing at least one target nerve; and
    an external RF power generator electrically connected to the ultrasound transducer device, the generator providing power to the ultrasound transducer device,
    wherein each of the plurality of transducer crystals has an angular sector cross-section, a curvilinear cross-section or a planar cross-section, and
    wherein each of the plurality of transducer crystals has a non-circular cross-section.

* * * * *